(12) United States Patent
Trail et al.

(10) Patent No.: US 10,843,011 B2
(45) Date of Patent: Nov. 24, 2020

(54) PARTICLE BEAM GUN CONTROL SYSTEMS AND METHODS

(71) Applicant: Varian Medical Systems, Inc., Palo Alto, CA (US)

(72) Inventors: Mark Everett Trail, Menlo Park, CA (US); James Edward Clayton, San Jose, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 15/657,036

(22) Filed: Jul. 21, 2017

(65) Prior Publication Data

US 2019/0022422 A1    Jan. 24, 2019

(51) Int. Cl.
*A61N 5/10* (2006.01)
*H01J 37/073* (2006.01)
(Continued)

(52) U.S. Cl.
CPC ............. *A61N 5/1077* (2013.01); *A61N 5/10* (2013.01); *H01J 37/073* (2013.01);
(Continued)

(58) Field of Classification Search
CPC .... A61N 5/1077; H01J 37/075; H01J 37/073; H05H 9/00
See application file for complete search history.

(56) References Cited

U.S. PATENT DOCUMENTS 4,737,680 A * 4/1988 True ................. H01J 1/46
313/348
4,998,073 A * 3/1991 Miyata ............. H05H 7/06
315/5.12
(Continued)

FOREIGN PATENT DOCUMENTS

EP    2108401 A1    11/2008
EP    2810693 A2    10/2014
(Continued)

OTHER PUBLICATIONS

Schüler, Emil, et al. "Experimental platform for ultra-high dose rate FLASH irradiation of small animals using a clinical linear accelerator." International Journal of Radiation Oncology* Biology* Physics 97.1 (2017): 195-203 (Year: 2017).*
(Continued)

*Primary Examiner* — Wyatt A Stoffa

(57) ABSTRACT

Presented systems and methods facilitate efficient and effective monitoring of particle beams. In some embodiments, a radiation gun system comprises: a particle beam gun that generates a particle beam, and a gun control component that controls the gun particle beam generation characteristics, including particle beam fidelity characteristics. The particle beam characteristics can be compatible with FLASH radiation therapy. Resolution control of the particle beam generation can enable dose delivery at an intra-pulse level and micro-bunch level. The micro-bunch can include individual bunches per each 3 GHz RF cycle within the 5 to 15 μsec
(Continued)

pulse-width. The FLASH radiation therapy dose delivery can have a bunch level resolution of approximately $4.4 \times 10^{-6}$ cGy/bunch.

13 Claims, 5 Drawing Sheets

(51) Int. Cl.
   *H01J 37/075*  (2006.01)
   *H05H 9/00*    (2006.01)
   *H01J 37/147*  (2006.01)

(52) U.S. Cl.
   CPC ............ *H01J 37/075* (2013.01); *H05H 9/00* (2013.01); *A61N 5/1081* (2013.01); *A61N 2005/1088* (2013.01); *H01J 37/1472* (2013.01)

(56) References Cited

U.S. PATENT DOCUMENTS

| | | |
|---|---|---|
| 5,834,787 A | 11/1998 | Bunker |
| 6,580,084 B1 | 6/2003 | Hiramoto et al. |
| 6,888,832 B2 | 5/2005 | Richardson et al. |
| 6,920,202 B1 | 7/2005 | Dinsmore |
| 7,423,278 B2 | 9/2008 | Amaldi et al. |
| 7,554,275 B2 | 6/2009 | Amaldi |
| 7,778,691 B2 | 8/2010 | Zhang et al. |
| 8,071,966 B2 | 12/2011 | Kaiser et al. |
| 8,121,253 B2 | 2/2012 | Nelms |
| 8,253,121 B2 | 8/2012 | Gnutzmann et al. |
| 8,405,056 B2 | 3/2013 | Amaldi et al. |
| 8,406,844 B2 | 3/2013 | Ruchala et al. |
| 8,618,521 B2 | 12/2013 | Loo et al. |
| 8,636,636 B2 | 1/2014 | Shukla et al. |
| 8,644,571 B1 | 2/2014 | Schulte et al. |
| 8,699,664 B2 | 4/2014 | Otto et al. |
| 8,798,343 B2 | 8/2014 | Kabus et al. |
| 8,901,519 B2 | 12/2014 | Schardt et al. |
| 8,986,186 B2 | 3/2015 | Zhang et al. |
| 9,018,603 B2 | 4/2015 | Loo et al. |
| 9,033,859 B2 | 5/2015 | Fieres et al. |
| 9,149,656 B2 | 10/2015 | Tanabe |
| 9,636,525 B1 | 5/2017 | Sahadevan |
| 2002/0030164 A1 | 3/2002 | Akiyama et al. |
| 2002/0057760 A1 | 5/2002 | Carroll et al. |
| 2006/0193435 A1 | 8/2006 | Hara et al. |
| 2006/0231775 A1* | 10/2006 | Harada ............ A61N 5/10 250/492.3 |
| 2006/0274061 A1 | 12/2006 | Wang et al. |
| 2007/0034812 A1 | 2/2007 | Ma et al. |
| 2008/0049897 A1 | 2/2008 | Molloy |
| 2008/0226030 A1 | 9/2008 | Otto |
| 2009/0026912 A1* | 1/2009 | Lordi ............ H01J 37/045 313/414 |
| 2009/0283702 A1 | 11/2009 | Umezawa et al. |
| 2010/0003770 A1 | 1/2010 | Shibata et al. |
| 2010/0195793 A1 | 8/2010 | Nelms |
| 2010/0288945 A1 | 11/2010 | Gnutzmann et al. |
| 2010/0327785 A1* | 12/2010 | Crewson ............ H05H 9/00 315/505 |
| 2011/0006214 A1 | 1/2011 | Boenig |
| 2011/0168903 A1 | 7/2011 | Kyele et al. |
| 2012/0134470 A1 | 5/2012 | Shibuya et al. |
| 2012/0136194 A1 | 5/2012 | Zhang et al. |
| 2012/0253495 A1 | 10/2012 | Wright et al. |
| 2013/0172658 A1 | 7/2013 | Brahme et al. |
| 2013/0231516 A1* | 9/2013 | Loo ............ A61N 5/1043 600/1 |
| 2014/0152176 A1* | 6/2014 | Chang ............ H01J 25/10 315/14 |
| 2014/0265823 A1 | 9/2014 | Boisseau et al. |
| 2014/0270086 A1 | 9/2014 | Krasnykh |
| 2015/0011817 A1 | 1/2015 | Feng |
| 2015/0057484 A1 | 2/2015 | Amaldi |
| 2015/0087882 A1 | 3/2015 | Pausch et al. |
| 2015/0094838 A1 | 4/2015 | MacLaverty |
| 2015/0117616 A1 | 4/2015 | Ishii et al. |
| 2015/0306423 A1 | 10/2015 | Bharat et al. |
| 2016/0193482 A1 | 7/2016 | Fahrig et al. |
| 2016/0225477 A1 | 8/2016 | Banine et al. |
| 2016/0287905 A1 | 10/2016 | Liger |
| 2016/0310764 A1 | 10/2016 | Bharadwaj et al. |
| 2017/0028220 A1 | 2/2017 | Schulte et al. |
| 2017/0203125 A1 | 7/2017 | Amato et al. |
| 2018/0235554 A1 | 8/2018 | Burgett |

FOREIGN PATENT DOCUMENTS

| | | |
|---|---|---|
| EP | 2805745 | 11/2014 |
| EP | 2979728 | 2/2016 |
| EP | 3043863 A1 | 7/2016 |
| EP | 3103519 A1 | 12/2016 |
| JP | 2014161706 A | 9/2014 |
| JP | 2017098000 A | 6/2017 |
| WO | 2006005059 | 12/2006 |
| WO | 2009042952 A1 | 4/2009 |
| WO | 2010088442 A1 | 8/2010 |
| WO | 2012135196 A1 | 10/2012 |
| WO | 2013038240 A1 | 3/2013 |
| WO | 2014139493 | 9/2014 |
| WO | 2015038832 A1 | 3/2015 |
| WO | 2015077881 A1 | 4/2015 |
| WO | 2015153746 A1 | 10/2015 |
| WO | 2016094284 A1 | 6/2016 |
| WO | 2016094284 A9 | 6/2016 |

OTHER PUBLICATIONS

Favaudon, Vincent, et al. "Ultrahigh dose-rate FLASH irradiation increases the differential response between normal and tumor tissue in mice." Science translational medicine6.245 (2014): 245ra93-245ra93. (Year: 2014).*

Harris, J. R., et al. "Longitudinal density modulation and energy conversion in intense beams." Physical Review E 76.2 (2007): 026402 (Year: 2007).*

H. Paganetti et al., "Proton Beam Radiotherapy—The State of the Art," New Technologies in Radiation Oncology (Medical Radiation Series), Springer Verlag, Heidelberg, ISBN 3-540-00321-5, Oct. 2005, 36 pages.

Qiyong Fan, Akshay Nanduri, Samuel Mazin, Lei Zhu, "Emission guided radiation therapy for lung and prostate cancers: A feasibility study on a digital patient", Med. Phys. 39 (11), Nov. 2012, 0094-2405/2012/39(11)/7140/13, 13 pages.

Radiotherapy "flashes" to reduce side effects, an effect for each mode of administration, Images of tissue sections, Ultra-high dose-rate, Science Translational Medicine, Jul. 16, 2014, 3 pages.

To introduce the concept of pseudo beam's-eye-view (pBEV), to establish a framework for computer-assisted beam orientation selection in intensity-modulated radiation therapy(IMRT), and to evaluate the utility of the proposed techniquie, Dec. 1, 2001 vol. 51, Issue 5, 3 pages, Pseudo beam's-eye-view as applied to beam orientation selection in intensity-modulated radiation therapy.

Wen C. His, Michael F. Moyers, Dmitri Nichporov, Vladimir Anferov, Mark Wolanski, Chris E. Allgower, Jonathan B. Farr, Anthony E. Mascia, Andreis N. Schreuder, "Energy spectrum control for modulated proton beams", Medical Physics, (2009) 36(6) 2297-2308, http://www.ncbi.nlm.nih.gov/pmc/articles/PMC2832068/.

V. Anferov, M. Ball, G.P. Berg, B. Broderick, J. Collins, G. East, D. Friesel, D. Jenner, W.P. Jones, J. Katuin, S. Klein, C. Nelson, N. Schreuder, Wm. Starks, J. Self, "The Indiana University Midwest Proton Radiation Institute", Proceedings of the 2001 Particle Accelerator Conference, (2001) p. 645-64 https://accelconf.web.cern.ch/accelconf/p01/PAPERS/FOAA004.PDF.

Th. Haberer,W. Becher,D. Schardt,G. Kraft "Magnetic scanning system for heavy ion therapy" Nuclear Instruments and Methods in Physics Research Section A: Accelerators, Spectrometers, Detectors

(56) References Cited

OTHER PUBLICATIONS and Associated Equipment , NIM , Elsevie, Jun. 10, 1993, vol. 330, Issues 1-2, Jun. 10, 1993, pp. 296-305.
Amaldi, TERA Foundation, Novara, Italy A. Degiovanni, CERN, Geneva, Switzerland Linac 2014. Proton and Carbon Linacs for Hadron Therapy U. http://accelconf.web.cern.ch/AccelConf/LINAC2014/papers/friob02.pdf.
Montay-Gruel P, Petersson K, Jaccard M, Boivin G, Germond JF, Petit B, Doenlen R, Favaudon V, Bochud F, Bailat C, Bourhis J, Vozenin MC. Irradiation in a flash: Unique sparing of memory in mice after whole brain irradiation with dose rates above 100Gy/s. Radiother Oncol. May 22, 2017. pii: S0167-8140(17)30365-1. doi: 10.1016/j.radonc.2017.05.003. [Epub ahead of print] PubMed PMID: 28545957.
Favaudon V, Caplier L, Monceau V, Pouzoulet F, Sayarath M, Fouillade C, Poupon MF, Brito I, Hupé P, Bourhis J, Hall J, Fontaine JJ, Vozenin MC. Ultrahigh dose-rate FLASH irradiation increases the differential response between normal and tumor tissue in mice. Sci Transl Med. Jul. 16, 2014;6(245):245ra93. doi: 10.1126/scitranslmed.3008973. PubMed PMID: 25031268.
Loo BW, Schuler E, Lartey FM, Rafat M, King GJ, Trovati S, Koong AC, Maxim PG. Delivery of Ultra-Rapid Flash Radiation Therapy and Demonstration of Normal Tissue Sparing After Abdominal Irradiation of Mice. International Journal of Radiation Oncology Biology Physics. vol. 98 Issue: 2 pp. E16-E16 Supplement: S Meeting Abstract: P003 Published: Jun. 1, 2017.
M. Bopp, H. Fitze, P. Sigg, and L. Stingelin "Upgrade concepts of the PSI accelerator RF systems for a projected 3 mA operation", Citation: AIP Conference Proceedings 600, 300 (2001); doi: 10.1063/1.1435259.
S. Benedetti, A. Grudiev, and A. Latina Phys. Rev. Accel. Beams 20, 040101—Published Apr. 13, 2017.
Z. Li, et. al., Normal conducting cw transverse crab cavity for producing short pulses in spear3, Proceedings of IPAC2017, Copenhagen, Denmark.
Valery Dolgashev, Sami Tantawi, Yasuo Higashi, Bruno Spataro, "Geometric dependence of radio-frequency breakdown in normal conducting accelerating structures," Applied Physics Letters, vol. 97, Issue 17, pp. 171501-171501-3, Oct. 2010.
Lisa Laurent, Sami Tantawi, Valery Dolgashev, Chris Nantista, Yasuo Higashi, Markus Aicheler, Samuli Heikkinen, and Walter Wuensch, Experimental Study of RF Pulsed Heating Phys. Rev. ST Accel. Beams 14, 041001 (2011) [21 pages].
S. Tantawi, Z. Li , patent pending, Title: "Distributed Coupling and Multi-Frequency Microwave Accelerators", filed Jul. 9, 2014, U.S. Appl. No. 62/022,469.
S.Tantawi , M.Nasr, "Designs and High Power Tests of Distributed Coupling Linacs" IFIC, Jun. 13-16, 2017 , Valencia , Spainhttps://indico.cern.ch/event/589548/contributions/2615455/attachments/1479738/2294080/Mamdouh_High_Gradient_2017.pdf.
Jensen, Aaron, Jeff Neilson, and Sami Tantawi. "X-band multi-beam klystron design and progress report." Vacuum Electronics Conference (IVEC), 2015 IEEE International. IEEE, 2015.
K.Halbach, "Design of permanent multipole magnets with oriented rare earth cobalt material", Nuclear Instruments and Methods , vol. 169, Issue 1, Feb. 1, 1980, pp. 1-10 [http://www.sciencedirect.com/science/article/pii/0029554X80900944].
J. K. Lim, P. Frigola, G. Travish, J. B. Rosenzweig, S. G. Anderson, W. J. Brown, J. S. Jacob, C. L. Robbins, and A. M. Tremaine, "Adjustable, short focal length permanent-magnet quadrupole based electron beam final focus system" Phys. Rev. ST Accel. Beams 8, 072401—Published Jul. 15, 2005.
Sayyed Bijan Jiaa, Mohammad Hadi Hadizadeha, Ali Asghar Mowlavi ,Mandy Ebrahimi Loushab "Evaluation of energy deposition and secondary particle production in proton therapy of brain using a slab head phantom" Elsevier , Reports of Practical Oncology & Radiotherapy,vol. 19, Issue 6, Nov.-Dec. 2014, pp. 376-384.
J. Perl, J Shin, J Schümann, B Faddegon and H Paganetti, "TOPAS—An innovative proton Monte Carlo platform for research and clinical applications," Med. Phys. 39:6818-6837, 2012, PMID: 23127075, PMID: 23127075.
Lisa Polster, Jan Schuemann, Ilaria Rinaldi, Lucas Burigo, Aimee Louise McNamara, Robert D Stewart, Andrea Attili, David J. Carlson, Alejandro Carabe-Femadez, Bruce Faddegon, Joseph Perl, and Harald Paganetti, "Extension of TOPAS for the simulation of proton radiation on molecular and cellular endpoints," Phys Med Biol. Jun. 10, 2015;60 (13):5053-5070, PMID: 26061583.
U. Amaldi et al., "Cyclinacs: Fast-Cycling Accelerators for Hadrontherapy," Nuclear Inst. and Methods in Physics Research, Mar. 2009.
S. Verdú-Andrés et al., "CABOTO, a high-gradient linac for hadrontherapy," Journal of Radiation Research, 2013, 54, pp. i155-i161.
A. Degiovanni et al., "Design of a Fast-Cycling High-Gradient Rotating Linac for Protontherapy," Proceedings of IPAC2013, Shanghai, China, THPWA008, 2013, pp. 3642-3644.
S. Verdú-Andrés et al., "Feasibility Study of a High-Gradient Linac for Hadrontherapy," Proceedings of IPAC2011, San Sebastián, Spain, WEPS045, 2011, pp. 2589-2591.
Bashkirov et al., "Development of proton computed tomography detectors for applications in hadron therapy", NIM Nuclear Instruments and Methods in Physics Research A (under press a the time of writing proposal) http://www.sciencedirect.com/science/article/pii/S0168900215009274 (abstract), vol. 809, Feb. 11, 2016, pp. 120-129, Elsevier.
Peach et al., "Pamela—A Model for an FFAG Based Hadron Therapy Machine", Proceedings of PAC07, Albuquerque, New Mexico, USA, IEEE, 2007, pp. 2880-2882.
Favaudon et al., "Ultrahigh dose-rate FLASH irradiation increases the differential response between normal and tumor tissue in mice", www.ScienceTranslationalMedicine.org, Jul. 16, 2014, vol. 6 Issue 245 245ra93, 9 pages.
Chang, Sha, "Compensator-intensity-modulated Radiotherapy—A traditional tool for modern application," US Oncological Disease 115 (2006): 1-4 (Year: 2006).

\* cited by examiner

PARTICLE BEAM GUN CONTROL SYSTEMS AND METHODS

FIELD OF THE INVENTION

The present invention relates to the field of particle beam radiation. In some embodiments, radiation systems and methods facilitate fast and effective generation of particle beams.

BACKGROUND

Particle beam radiation can be utilized in a number of different applications and accurately applying an appropriate amount of radiation can be very important. It is often critical to apply an accurate dose of particle beam radiation in medical therapy applications. Particle beam radiation therapy typically includes directing a beam of particles (e.g., ionizing particles, protons, etc.) at an area of tissue. The particles are usually associated with or include a charge. The particles are typically used to stop the growth or spread of the targeted tissue cells by killing them or degrading their cell division ability. While particle beam radiation is generally considered beneficial, there can be a number of potential side effects. The side effects can include unintended damage to DNA of healthy tissue cells. The effectiveness of particle beam radiation is primarily a function of the dose or amount of charged particles that is applied to cancerous cells while avoiding impacts to healthy cells.

The amount of charged particles that are applied to the tissue is typically a function of a dose rate or "current" of charged particles and time the targeted tissue is exposed to the radiation. Faster dose rates usually enable shorter exposure times and that can have a number of benefits, including less opportunity for extraneous events to influence the therapy, increased productivity, and greater convenience to the patient. One approach includes an ultra-high dose rate treatment or modality referred to as FLASH radiotherapy. Therapeutic windows associated with FLASH therapy often enable reduced normal tissue toxicity while maintaining cancerous tissue tumor control. However, these therapeutic windows are usually very narrow or precise and exposure outside the windows can be very detrimental to otherwise healthy tissue. Developing systems and methods to deliver dose rates typically associated with FLASH therapies can be difficult and problematic. Conventional attempts with pulse dropping and servoing are usually too coarse and cannot provide adequate resolution and fidelity.

SUMMARY

Presented systems and methods facilitate efficient and effective monitoring of particle beams. In some embodiments, a radiation gun system comprises: a particle beam gun that generates a particle beam, and a gun control component that controls the gun particle beam generation characteristics, including particle beam fidelity characteristics. The particle beam characteristics can be compatible with FLASH radiation therapy. Resolution control of the particle beam generation can enable dose delivery at an intra-pulse level and micro-bunch level. The micro-bunch can include individual bunches per each three GHz RF cycle within the 5 to 15 µsec pulse-width. The FLASH radiation therapy dose delivery can have a bunch level resolution of approximately $4.4 \times 10^{\wedge} - 6 cGy/bunch$.

The radiation gun system particle beam gun can include a photocathode gun and a bend magnet, and the control component includes a laser component. The photocathode gun can be integral part of a first short linear accelerator and is operable to emit electrons when excited by the laser. The bend magnet can be operable to bend the electrons and provide a line-of-site path for the exciting laser to the photo-cathode, the resulting bent beam is then forwarded into a second linear accelerator to accelerate the beam to it's final energy. The laser component can be operable to control "gating" or switching on and off of the electron emission from the gun. A 5 µsec pulse can corresponds to ~15 K e-bunches, which are gated utilizing the gating function of the photocathode injector to the control the dose output approximating a resolution of dose per bunch.

An alternate method, which enables a coarser dose control fidelity compared to the photo cathode, is to utilize a gridded electron gun with fast gating electronics. With some embodiments, the gating can be initiated within the middle or flatter portion of the pulse reducing energy spread associated with transients of the pulse rise/fall times. The fast gating can be achieved via a gun driver capable of gating on and off quickly at a rate that enables bunch-gating resolution. The on/off gating can be at a rate of 333 psec.

In some embodiments, a radiation method comprises: pulsing particle generation in a radiation therapy system at a periodic rate, wherein the pulsing has characteristics compatible with ultra high dose rates; accelerating the particles in a beam through a linear accelerator; and directing the beam emission at a target. The pulsing can be in a microwave range. The pulsing can have high fidelity characteristics. The particle beam characteristics can be compatible with FLASH radiation therapy. The resolution control of particle beam generation can approach the micro-bunch level In some embodiments, a radiation therapy system comprises: a beam generation system that generates and transports a beam of particles; a nozzle that aims the beam toward various locations within an object; and a control component that receives and directs execution of a prescribed treatment plan. In some exemplary implementations, the beam generation system includes: a particle beam gun that generates a particle beam, and a gun control component that controls the gun particle beam generation characteristics, including particle beam fidelity characteristics. The particle beam characteristics are compatible with FLASH radiation therapy. The beam generation system can include a liner accelerator and includes components that direct a particle beam in a direction toward and into the nozzle the nozzle may be mounted on or a part of a fixed, rotating or movable gantry so that it can be moved relative to the supporting device. The gun subsystem can enable high resolution control of particle beam generation.

BRIEF DESCRIPTION OF THE DRAWINGS

The accompanying drawings together with the description are incorporated in and form a part of this specification. They illustrate exemplary embodiments and explain exemplary principles of the disclosure. They are not intended to limit the present invention to the particular implementations illustrated therein. The drawings are not to scale unless otherwise specifically indicated

DETAILED DESCRIPTION OF THE INVENTION

Reference will now be made in detail to the preferred embodiments of the invention, examples of which are illustrated in the accompanying drawings. While the invention will be described in conjunction with the various embodiments, it will be understood that they are not intended to limit the invention to the various embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one ordinarily skilled in the art that the present invention may be practiced without these specific details. In other instances, well known methods, procedures, components, and circuits have not been described in detail as not to unnecessarily obscure aspects of the current invention.

Presented systems and methods facilitate efficient and effective control of photon beam generation. In some embodiments, particle beam generation control facilitates ultra high radiation dose rates with high fidelity delivery. The systems and methods are compatible with pulse width modulation. In some exemplary implementations, timing control resolution is configured to facilitate delivery fidelity approaching intra-pulse and micro-bunch levels. A micro-bunch level can correspond to individual bunches per radio frequency cycle in a pulse width. The radio frequency can be in the microwave range. In some exemplary implementations, a presented system and method can be utilized in FLASH radiation therapy applications. The systems and methods are also compatible with multiple field treatment approaches and can enable dose delivery for each faction/field to be effectively controlled.

Figure 1:
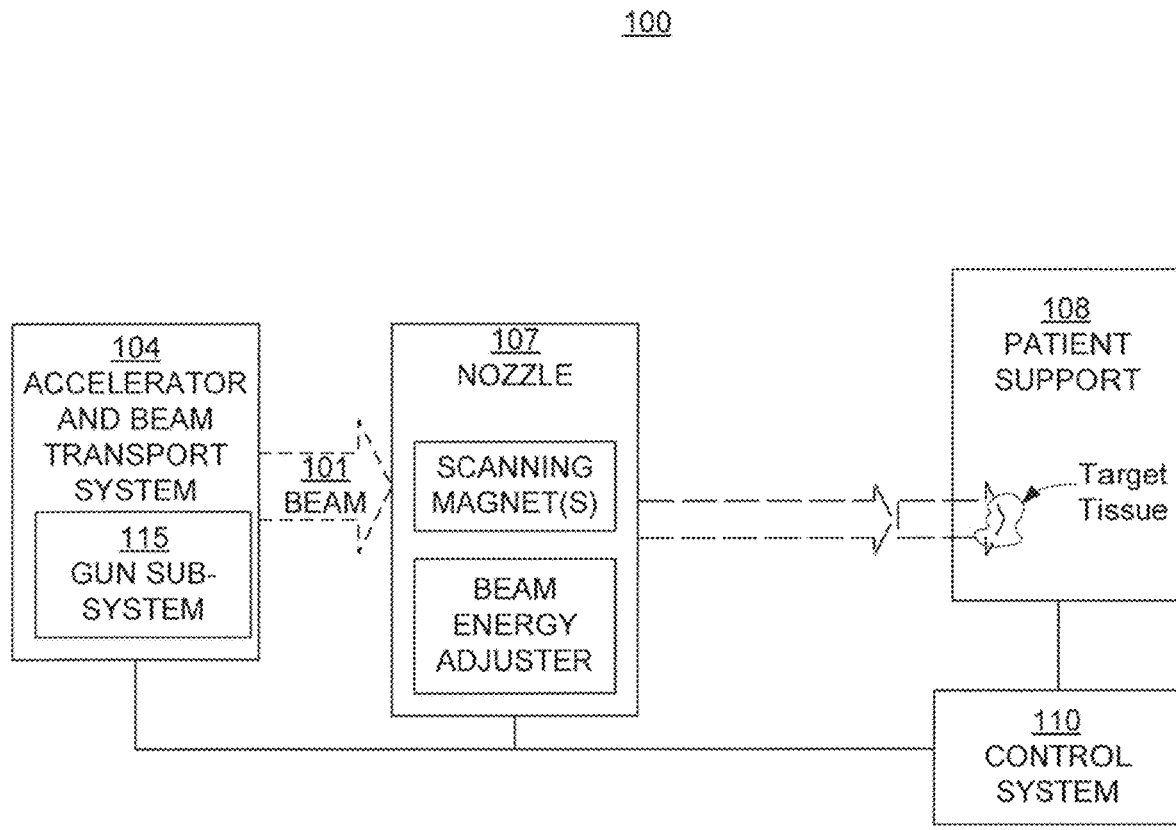
FIG. 1 is a block diagram of an exemplary radiation system in accordance with some embodiments.

FIG. 1 is a block diagram of an exemplary radiation therapy system 100 in accordance with some embodiments. Radiation therapy system 100 includes a beam generation system 104, a nozzle 107, and control system 110. The beam generation system 104 generates and transports a beam of particles (e.g., electrons, protons, neutrons, photons, ions, etc.). In some embodiments, the plurality of particles are travelling in substantially the same direction. In some exemplary implementations, particles traveling in substantially the same direction are included in a beam. The beam can be an atom nuclei beam (e.g., from carbon, helium, lithium, etc.). The beam can be considered a relatively well-defined beam.

In some embodiments, the beam generation system 104 includes a particle accelerator. The particle accelerator can include a liner accelerator. The system is compatible with a variety of accelerators (e.g., a continuous wave beam proton accelerator, an isochronous cyclotron, a pulsed proton accelerator, a synchrocyclotron, a synchrotron, etc.). In some embodiments, the accelerator is capable of relatively continuous wave output and extracts particles with a specified energy. This can provide a high, continuous wave beam current for the high dose rate per shot or treatment application. A shot is the dose delivered in a relatively short period of time along a line segment through the target tissue. Shots can be included in a scan pattern and independently adjusted (e.g., in intensity, in range, etc.) to irradiate a target tissue volume. The accelerator can be a lower power output cyclotron, such as a cyclotron that accelerates particles to the range of 70-300 MeV. The primary particle beam generator may be configured to correlate the time of the secondary photon emission with the particle beam generation (e.g., to further improve signal-to-noise ratio, etc.).

Beam generation system 104 includes gun subsystem 115. Gun subsystem 115 enables high resolution control of particle beam generation. In some embodiments, gun subsystem 115 is compatible with timing control of particle beam generation operations a microwave frequency range. Gun subsystem 115 can be utilized in a radiation therapy system to deliver FLASH radiation therapy. Additional description of gun-subsystems is presented in later portions of this specification.

The beam generation system 104 can include various other components (e.g., dipole magnets, bending magnets, etc.) that direct (e.g., bend, steer, guide, etc.) the beam through the system in a direction toward and into the nozzle 107. The beam generation system 104 may also include components that are used to adjust the beam energy entering the nozzle 107. In some embodiments, sets of quadrupole magnets are located along the beam paths in the beam generation system 104. In some exemplary implementations, the radiation therapy system may include one or more multileaf collimators (MLCs). A MLC leaf can be independently moved back-and-forth by the control system 110 to dynamically shape an aperture through which the beam can pass. The aperture can block or not block portions of the beam and thereby control beam shape and exposure time.

The nozzle 107 can be used to aim the beam toward various locations within an object (e.g., a patient, target tissue, etc.). The object can be located on the supporting device 108 (e.g., a chair, couch, bench, table, etc.) in a treatment room. The nozzle 107 may be mounted on or a part of a fixed, rotating or movable gantry (not shown) so that it can be moved relative to the supporting device 108. The supporting device may also be moveable. In some embodiments, the beam generation system 104 is also mounted on or is a part of the gantry. In some other embodiments, the beam generation system is separate from the gantry. In some exemplary implementations, a separate beam generation system is in communication with the gantry.

In some embodiments, control system 110 receives and directs execution of a prescribed treatment plan. In some exemplary implementations, the control system 110 includes a computer system having a processor, memory, and user interface components (e.g. a keyboard, a mouse, a display, etc.). The control system 110 can control parameters of the beam generation system 104, nozzle 107, and supporting device 108, including parameters such as the energy, intensity, direction, size, and shape of the beam. The control system 110 can receive data regarding operation of the system 100 and control the components according to data it receives. The data can be included in the prescribed treatment plan. In some embodiments, the control system 110 receives information and analyzes the performance and treatment being provided by radiation therapy system 100. The monitor component can measure and track beam current and beam charge, which are used to draw a correlation with the dose rate and dose amount respectively. In some embodiments, control system 110 can direct adjustments to the radiation therapy system 100 bases upon the analysis of dose and dose rate.

As noted above, the particle beam entering the nozzle 107 can have a specified energy and the nozzle 107 includes one or more range shifting and modulating components that affect the energy of the beam. In some embodiments, the nozzle 107 includes components such as magnets that control (e.g., steer, guide, deflect, scan, etc.) the beam particles in "X and Y directions" to scan a target tissue volume. The target tissue volume can be in a patient on the supporting device 108. The nozzle 107 can also include a beam energy adjuster that affects the energy of the particle beam. In some exemplary implementations, adjustments in the particle beam energy can be used to control: the range of the beam (e.g., the extent that the beam penetrates target tissue, etc), the dose delivered by the beam, the depth dose curve of the beam, depending on the type of beam. For example, for a proton beam or an ion beam that has a Bragg peak, the beam energy adjuster can control the location of the Bragg peak in the target tissue. The beam energy adjuster can include various components (e.g., range modulators, range shifters, etc.). The beam system 104 may also include components that are used to adjust the beam energy entering the nozzle 107.

Radiation therapy system 100 can be utilized for high dose rate treatments. Some treatment approaches include ultra-high dose rate treatment or modality referred to as FLASH radiotherapy. Therapeutic windows associated with FLASH therapy often enable reduced normal tissue toxicity while maintaining cancerous tissue tumor control. In some exemplary implementations, the FLASH radiotherapy dose rate can be at least 4 Gray (Gy) in less than one second and as much as 20 Gy or 40 Gy in less than a second. In some exemplary implementations, the FLASH radiotherapy dose rate can be more than 40 Gy in less than one second. The radiation therapy systems and methods are also compatible with multiple field treatment approaches in which different fields are associated with a particular treatment trajectory and a dose per field that is a portion or fraction of a total dose delivery.

Figure 2:
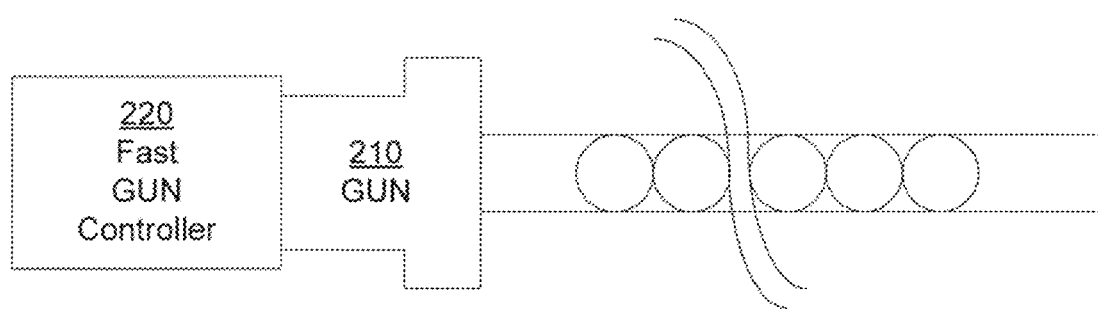
FIG. 2 is a block diagram of a gun subsystem in accordance with some embodiments.

FIG. 2 is a block diagram of a gun subsystem 200 in accordance with some embodiments. Gun subsystem is similar to gun subsystem 115 and can be utilized in a radiation therapy system to deliver FLASH radiation therapy. Gun subsystem 200 includes gun control component 210 and gun 220. Gun 220 generates a particle beam. It is appreciated that gun 220 can be a variety of different gun types. Gun control component 210 controls the gun particle beam generation characteristics, including particle beam fidelity characteristics.

Particle beam fidelity can facilitate utilization of various treatment features. The treatment features or characteristics can include high dose rates, multiple field treatment plans, Intensity Modulated Radio Therapy (IMRT), and so on. High dose rate approaches can facilitate delivery of a prescribed dose very rapidly, thereby reducing the radiation exposure time window and opportunity for undesirable movement of the target tissue. Faster delivery can also reduce discomfort and inconvenience to a patient. Multiple field treatment plans can be used in which different fields are associated with a particular treatment trajectory and a dose per field that is a portion or fraction of a total dose delivery. Delivering a fraction of a dose per field typically results in a reduced exposure time interval per field treatment. It is appreciated that a number of treatment plans can be associated with fine or very small radiation exposure timing intervals. Applying multiple treatment approaches together (e.g., ultra high dose rate in multiple fields) can result in radiation exposure windows being very small (e.g., a fraction of a fraction of a second, etc.).

Gun control component 210 can facilitate particle beam generation that has timing resolutions and fidelity characteristics compatible with very short radiation exposure intervals. In some embodiments, a gun subsystem is configured to control particle beam generation timing intervals associated with delivery of a field dose fraction at a high dose rate. In some exemplary implementations, a gun-subsystem can control particle beam generation in accordance with pulse width modulation techniques. In some embodiments, a dose can be delivered over a few pulses depending on pulse width and pulsed radio frequency fields (PRF).

In some embodiments, resolution control of particle beam generation can enable dose delivery at intra-pulse and micro-bunch levels. In some exemplary implementations, a micro-bunch level includes individual bunches per each 3 GHz RF cycle within a 5 to 15 μsec pulse-width. The ability to control dose delivery approaching the bunch level can improve resolution to approximately $4.4 \times 10^\wedge - 6 cGy/bunch$. It is appreciated that this resolution may be more than needed in some treatment plans. In some exemplary implementations, the resolution control facilitates approximately one percent control on the dose delivery. The treatment or dose resolution can be useful when implemented to arc treatments. It is appreciated a gun subsystem can include various implementations.

In some embodiments, the system can deliver 20 Gy/sec at 100 cm. The beam energy can be 20 MeV at a beam power of 10 kW with an average beam current of 0.5 mA and a peak beam current of 33 mA. It is appreciated that these values are exemplary. In some exemplary implementations, a system and method can operate within a range of these values (e.g., within 1%, within 5%, 5% to 20%, etc.).

Figure 3:
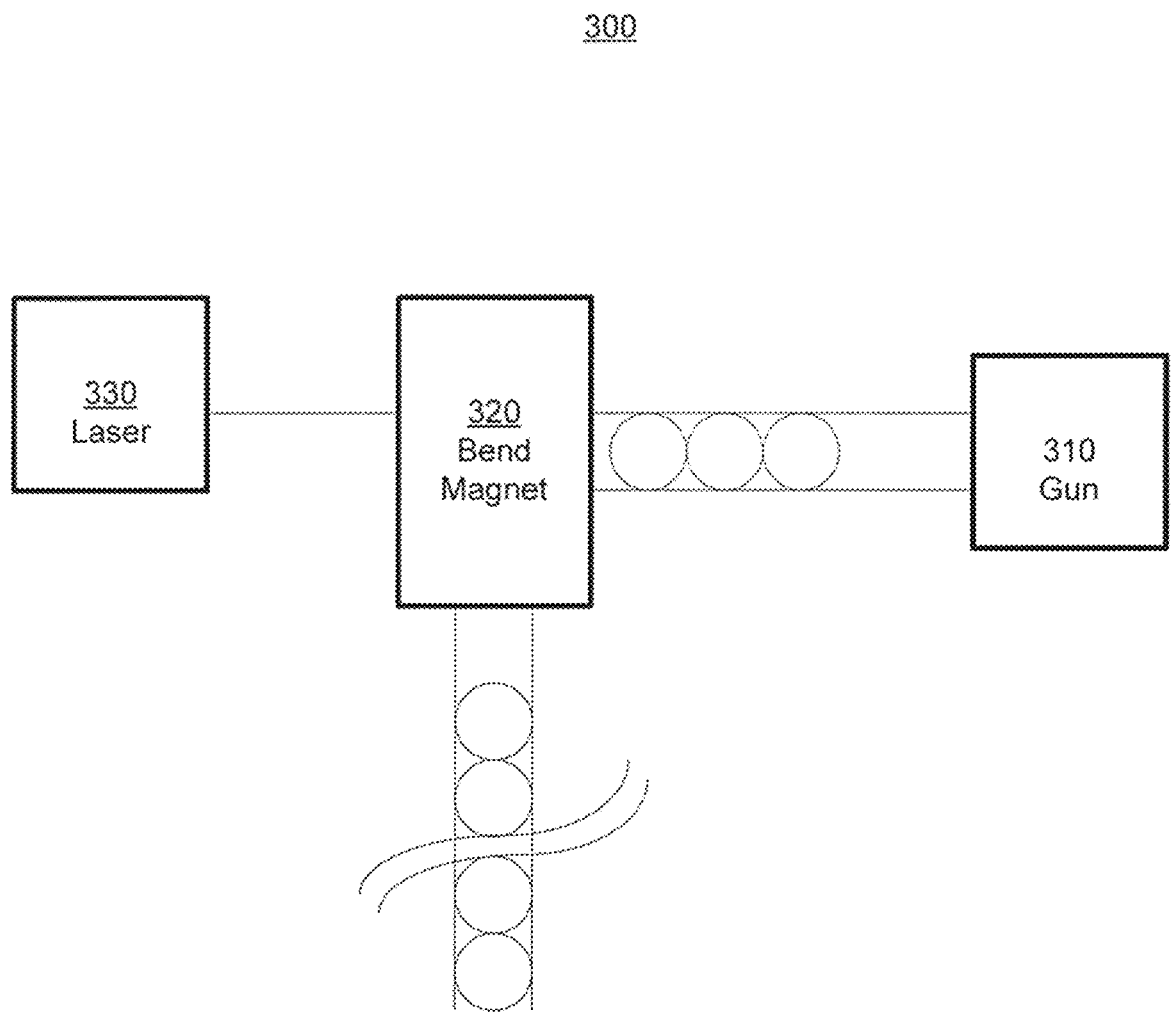
FIG. 3 is a block diagram of an exemplary laser controlled gun subsystem in accordance with some embodiments.

FIG. 3 is a block diagram of an exemplary laser controlled gun subsystem 300 in accordance with some embodiments. Gun subsystem 300 includes photocathode gun 310, a bend magnet 320, and laser component 330. Gun 301 includes a photocathode gun operable to emit electrons when excited by the laser. Gun 301 can be an integral part of a linear accelerator. The linear accelerator can have a first section and a second section with a bend component coupled between the sections. The bend component 320 is operable to bend the electrons accelerated by the gun-subsystem and the first linear accelerator section. The bend component can include a bend magnet that influences or directs the electrons through the bend. In some embodiments, the bend component 310 is configured to provide a line-of-site path for an exciting laser from laser component 330 to a photo-cathode included in gun component 310. The bent particle beam is directed into a second linear accelerator to accelerate the particle beam to its final energy. In some embodiments, the particle beam energy can be adjusted after the second linear accelerator.

The laser component 330 is operable to control "gating" or switching on and off of the electron emission from the gun. In some embodiments, a 5 μsec pulse corresponds to ~15K e-bunches, which can be turned on and off utilizing the on/off function of the photocathode injector to control the dose output approximating resolution of dose per bunch. In some embodiments, the laser is pulsed at frequencies in a microwave range. In some exemplary implementations, the oscillation is in the 3 GHz range. In some embodiments, the laser is pulsed away from the rise and fall transient parts of a waveform.

Figure 4:
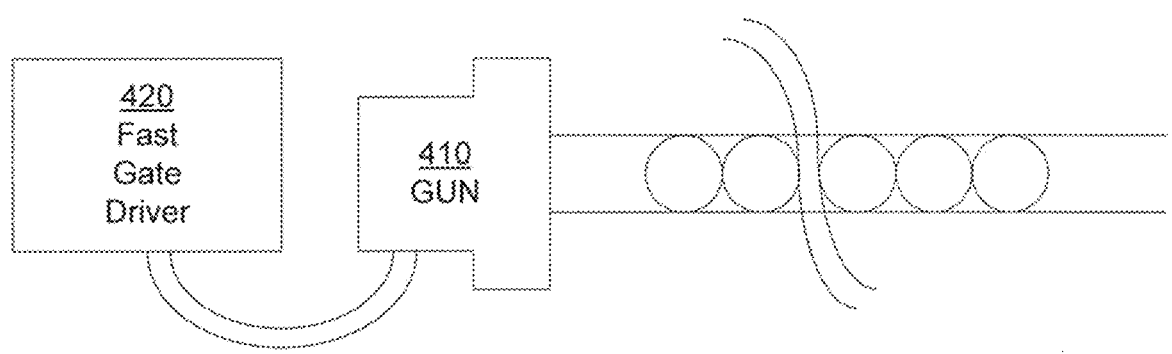
FIG. 4 is a block diagram of another exemplary driver controlled gun subsystem in accordance with some embodiments.

FIG. 4 is a block diagram of an exemplary driver controlled gun subsystem 400 in accordance with some embodiments. Gun subsystem 400 includes a gridded gun 410 and fast gun driver component 420. Fast gun driver component 420 is capable of gating a grid on and off as quickly as 333 psec, which in turn enables bunch gating resolution. In some embodiments, fast gun driver component 420 facilitates intra-pulse dose-delivery control.

Figure 5:
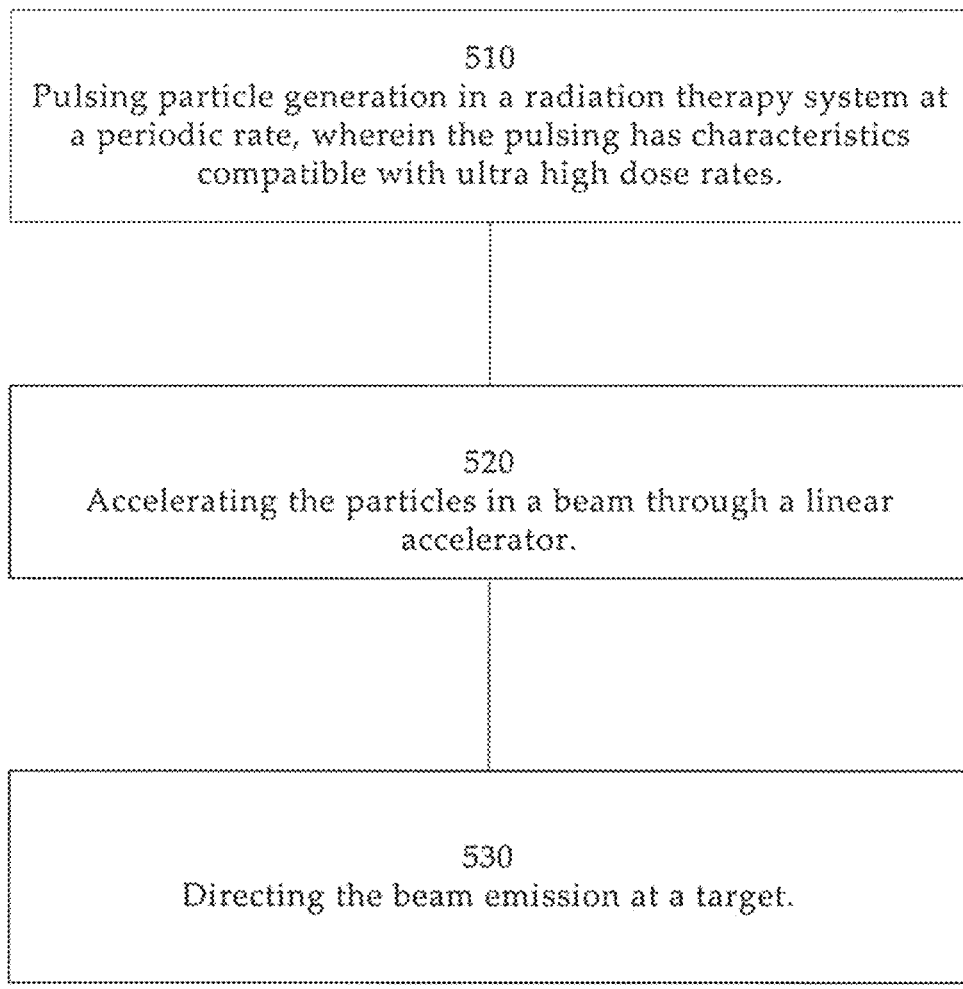
FIG. 5 is a block diagram of a particle beam generation method in accordance with some embodiments.

FIG. 5 is a block diagram of a particle beam generation method 500 in accordance with some embodiments.

In block 510, particle generation in a radiation therapy system is pulsed at a periodic rate. The pulsing can be in a microwave range. In some embodiments the pulsing has characteristics compatible with ultra high dose rates. The pulsing can have high fidelity characteristics.

In block 520, the particles are accelerated in a beam through a linear accelerator. In some embodiments, the linear accelerator includes a portion that accelerates the particles. In some exemplary implementations, the linear accelerator includes a portion that decelerates the particles.

In block 530, the beam emission is directed at a target. In some embodiments, the particle beam includes electrons that are directed at a target that emits photons and the photons are directed at target tissue. In some exemplary implementations, the particle beam includes electrons that are directed at the target tissue.

It is appreciated that in addition to medical applications, fast gun control may also have other applications such as industrial applications where high dose rates facilitate various characteristics (e.g., radiation hardening, cross-linking, etc.)

Thus, the presented systems and methods facilitate efficient and effective radiation beam generation. In some embodiments, a pulse width high dose rate control system and method enables improved fidelity over coarser traditional gun control pulse dropping and pulse servoing approaches.

Some portions of the detailed descriptions are presented in terms of procedures, logic blocks, processing, and other symbolic representations of operations on data bits within a computer memory. These descriptions and representations are the means generally used by those skilled in data processing arts to effectively convey the substance of their work to others skilled in the art. A procedure, logic block, process, etc., is here, and generally, conceived to be a self-consistent sequence of steps or instructions leading to a desired result. The steps include physical manipulations of physical quantities. Usually, though not necessarily, these quantities take the form of electrical, magnetic, optical, or quantum signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are associated with the appropriate physical quantities and are merely convenient labels applied to these quantities. Unless specifically stated otherwise as apparent from the following discussions, it is appreciated that throughout the present application, discussions utilizing terms such as "processing", "computing", "calculating", "determining", "displaying" or the like, refer to the action and processes of a computer system, or similar processing device (e.g., an electrical, optical or quantum computing device) that manipulates and transforms data represented as physical (e.g., electronic) quantities. The terms refer to actions and processes of the processing devices that manipulate or transform physical quantities within a computer system's component (e.g., registers, memories, other such information storage, transmission or display devices, etc.) into other data similarly represented as physical quantities within other components.

The foregoing descriptions of various specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as suited to the particular use contemplated. It is intended that the scope of the invention be defined by the claims appended hereto and their equivalents. The listing of steps within method claims do not imply any particular order to performing the steps, unless explicitly stated in the claim.

What is claimed:

1. A radiation gun system comprising:
a particle beam gun that generates a particle beam and is an integral part of a first short linear accelerator, wherein the particle beam gun includes a photocathode and a bend magnet; and
a gun control component that controls generation characteristics of the particle beam, including particle beam fidelity characteristics corresponding to a dose of rate of at least 20 Gy/second, wherein the gun control component includes a laser component operable to control switching on and off gating of electron emission from the photocathode in response to excitation by the laser component and the bend magnet is operable to bend the electrons and provide a line-of-site path for the laser to the photocathode, wherein a resulting bent beam is then forwarded into a second linear accelerator to accelerate the beam to its final energy.

2. The radiation gun system of claim 1, wherein resolution control by the gun control component of the particle beam generation enables dose delivery at an intra-pulse level.

3. The radiation gun system of claim 1, wherein resolution control by the gun control component of the on and off gating of electron emission from the photocathode enables dose delivery at a micro-bunch level.

4. The radiation gun system of claim 3, wherein the micro-bunch level includes individual bunches per each 3 GHz frequency cycle within a 5 to 15 μsec pulse-width.

5. The radiation gun system of claim 3, wherein the particle beam characteristics include configuring emitted electrons in electron bunches with a bunch level resolution of approximately $4.4 \times 10^{\wedge} - 6$ cGy/electron bunch.

6. The radiation gun system of claim 1, wherein in a 5 μsec pulse there are 15,000 on and off operations/bunch in a gating function of a photocathode injector to control a dose output corresponding to a resolution of dose per bunch.

7. The radiation gun system of claim 1, wherein the gating is initiated within the middle of the pulse reducing energy spread associated with transients of the pulse rise/fall times.

8. The radiation gun system of claim 1, wherein the particle beam gun is a gridded gun and the control component includes a gun driver that switches on and off at a rate that corresponds to a bunch resolution, wherein the bunch resolution defines an amount of electrons in a bunch and the gun driver on and off generates the amount of particles that corresponds bunch resolution.

9. The radiation gun system of claim 8, wherein gating is at 333 psec.

10. A radiation therapy system comprising:
a beam generation system that generates and transports a beam of particles, where the beam generation system includes:
   a particle beam gun that generates a particle beam, wherein the particle beam gun is a gridded gun; and
   a gun controller that controls generation characteristics of the particle beam, including particle beam fidelity characteristics, corresponding to a dose of rate of at least 20 Gy/second, wherein the gun control component includes a gun driver capable of gating on and off, and is configured to initiate the gating is within a middle of a pulse reducing energy spread associated with transients of pulse rise/fall times; and
   a control component that receives and directs execution of a prescribed treatment plan.

11. A radiation therapy system of claim 10, wherein the beam generation system includes a linear accelerator and components that direct a particle beam in a direction toward and into a nozzle.

12. A radiation therapy system of claim 11, wherein the nozzle may be mounted on or a part of a fixed, rotating or movable gantry so that it can be moved relative to a supporting device.

13. A radiation therapy system of claim 10, wherein the beam generation system enables high resolution control of particle beam generation.

* * * * *